Sept. 24, 1957 F. W. ANDERSON Plant Pat. 1,645

NECTARINE TREE

Filed Jan. 28, 1957

WITNESS

Addison E. Avery

INVENTOR

Frederic W. Anderson

BY Webster & Webster

ATTYS.

United States Patent Office

Plant Pat. 1,645
Patented Sept. 24, 1957

1,645

NECTARINE TREE

Frederic W. Anderson, Merced, Calif.

Application January 28, 1957, Serial No. 636,846

1 Claim. (Cl. 47—62)

Figure 1:
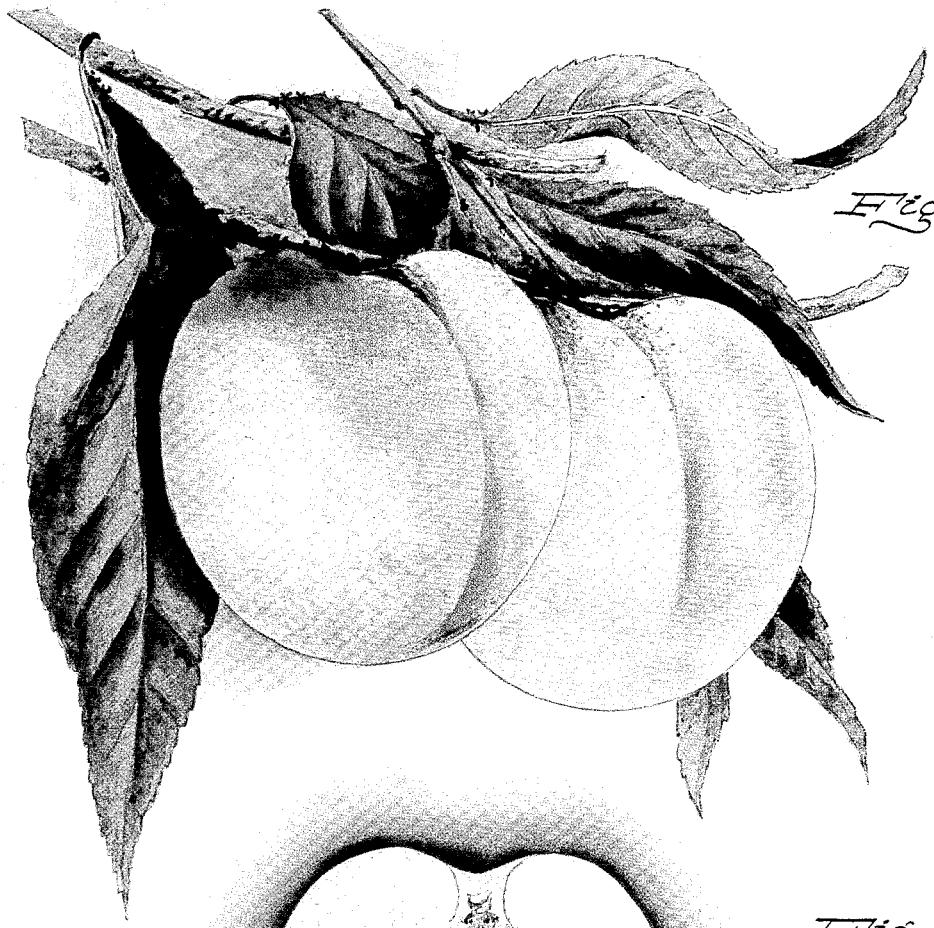

The present invention relates to a new and distinct variety of nectarine tree which bears large, highly colored, clingstone fruit.

This variety—while generally resembling the Early Le Grand nectarine (United States Plant Patent No. 980), especially in relation to ripening period and favorable market qualities—is improved, for commercial growing, in that it does not possess certain defects inherent in such Early Le Grand nectarine.

While the Early Le Grand nectarine has been very popular, both in domestic and export markets, production of fruit by the variety has been low following warm winters, as sometimes occur in the San Joaquin Valley of California, and wherein many nectarine orchards exist.

Further, humid weather during the ripening period has caused extensive skin cracking on the fruit of the Early Le Grand nectarine, and this—together with considerable split pits—has substantially reduced production of marketable fruit during some seasons.

To obtain a nectarine variety having substantially the same ripening period and the marketable fruit of the Early Le Grand nectarine, but without the noted defects, a large number of seedlings of various crosses were grown and fruited at my experimental orchard near Le Grand, Merced County, California; all under by direct control and observation. Of such seedlings one appeared to be of especial promise and it was selected for further testing, observation, and asexual reproduction; the selected variety being the one here claimed.

The present variety is an F–1 cross between the Le Grand nectarine (United States Plant Patent No. 549) and the Star Grand nectarine (United States Plant Patent No. 1327). Subsequent to its origination and selection the variety was asexually reproduced by me through the medium of buds top-worked on mature trees in my experimental orchard, as aforesaid, and these reproductions have fullly run true.

It was apparent that I had brought forward—in originating the instant variety—a nectarine tree that generally paralleled the Early Le Grand nectarine in ripening period and other desirable characteristics; one that does not possess the objectionable defects thereof; and one which substantially differs in the following characteristics:

The present variety of nectarine has a lower chilling requirement, as is evident by the fact that after recent relatively warm winters in the San Joaquin Valley of California, full crops have been borne on both the parent tree and the trees which were top-worked to the variety.

Also, the variety has consistently produced more marketable fruit in each harvest season; there having been only half as many culls from all causes, very few growth cracks or split pits, and considerably more red exterior color on a smoother surface.

Additionally, there are two qualitative differences which distinguish this variety from the Early Le Grand; to-wit, the flowers have petals which are of medium instead of large size, and the fruit has sweet instead of bitter kernels.

In the drawings:

Fig. 1. is a perspective view of two of the fruit, together with twigs and leaves.

Figure 2:
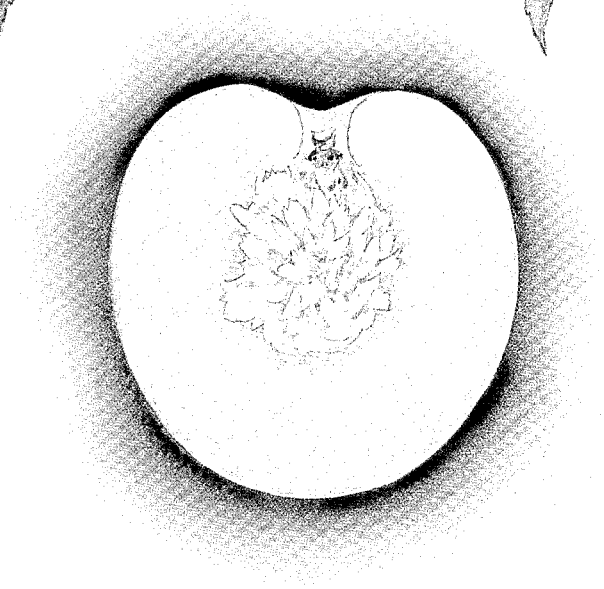

Fig. 2 is a sectional elevation of one of the fruit with the clingstone exposed; flesh being adherent to a major portion of said stone.

Referring now more specifically to the pomological details of this new and distinct variety of nectarine tree, the following is an outline description thereof; all major plate identifications being by reference to Maerz and Paul Dictionary of Color:

Tree:
- *Size.*—Medium.
- *Vigor.*—Vigorous.
- *Growth.*—Spreading.
- *Shape.*—Vase formed.
- *Production.*—Productive.
- *Bearing.*—Regular bearer.

Trunk: Size—medium.

Branches: Size—medium.

Leaves:
- *Size.*—Large. Average length, 6½″. Average width, 1¾″.
- *Margin.*—Glandular; crenate.
- *Petiole.*—Medium length.
- *Glands.*—Average number—five. Opposite; reniform. Position—usually two on petiole and two to four on blade.
- *Color.*—Top side—medium green (22–L–8). Under side—lighter green (22–J–6).

Flower Buds:
- *Size.*—Medium.
- *Length.*—Medium.

Flowers:
- *Date of first and full bloom.*—About with the Le Grand nectarine, and a few days before the Elberta peach.
- *Size.*—Medium.

Fruit:
- *Maturity when described.*—Eating ripe.
- *Date of first picking.*—July 11, 1956.
- *Date of last picking.*—July 21, 1956.
- *Size.*—Large, uniform. Average diameter axially, 2¾″. Average transversely in suture plane, 2⅝″.
- *Form.*—Uniform; globose.
- *Suture.*—Rather conspicious; distinct; deep; extends from base to apex.
- *Ventral surface.*—Rounded strongly; lips equal.
- *Cavity.*—Average depth, ⅜″. Average breadth, ¾″.
- *Base.*—Rounded.
- *Apex.*—Short; rounded.

Skin:
- *Thickness.*—Medium.
- *Texture.*—Medium.
- *Tendency to crack.*—Very slight.
- *Down.*—Wanting.
- *Color.*—Light yellow under-color (10–L–2), shading to a darker yellow (10–L–6), overspread with an orange-cast red (2–J–12), shading to a darker ruby red (6–L–6). In some specimens the red color only partially overspreads the yellow, and the latter shows to a substantial extent, while in other specimens the red color substantially entirely overspreads the fruit, and here such color is mainly of the orange-cast red.

Flesh:
- *Amygdalin.*—Scant.
- *Texture.*—Firm; meaty.
- *Ripens.*—Even.
- *Flavor.*—Sub-acid.

*Aroma.*—Distinct.
*Eating quality.*—Good to best.
*Color.*—A substantially jonquil yellow (9–J–5), shading to a corn yellow (10–J–5).

Stone:
*Type.*—Cling.
*Size.*—Medium. Average length, 1 5/16". Average breadth, 1 3/16". Average thickness, ¾".
*Form.*—Oval.
*Apex.*—Rounded.
*Sides.*—Equal.
*Surface.*—Irregularly furrowed near base; pitted throughout.
*Pits.*—Elongated.
*Ventral edge.*—Thick.
*Dorsal edge.*—Full, with deep narrow groove.
*Ridges.*—Continuous.
*Tendency to split.*—Very slight.
*Color.*—Brown (4–H–10).

Use: Market; local and long distance shipping.

Keeping quality: Good.
Shipping quality: Good.

The tree and its fruit herein described may vary in slight detail due to climatic and soil conditions under which the variety may be grown.

The following is claimed:

A new and distinct variety of nectarine tree, as illustrated and described, which bears large size, yellow flesh, clingstone fruit wherein the skin is a yellow ground color overspread with red; the fruit having general resemblance to the Early Le Grand nectarine and substantially the same harvest period, but is characterized—in comparison—by a lower chilling requirement, the regular bearing of larger crops with less culls due to growth cracks and split pits, more exterior red color on a smoother surface of the fruit, kernels which are sweet in flavor, and flowers having medium size petals.

No references cited.